US005582821A

United States Patent [19]
Kaye

[11] Patent Number: 5,582,821
[45] Date of Patent: Dec. 10, 1996

[54] METHODS FOR TREATING BLEEDING DISORDERS

[75] Inventor: James A. Kaye, Brookline, Mass.

[73] Assignee: Genetics Institute, Inc., Cambridge, Mass.

[21] Appl. No.: 278,765

[22] Filed: Jul. 22, 1994

[51] Int. Cl.⁶ .................................................. A61K 45/05
[52] U.S. Cl. .............................................................. 424/85.2
[58] Field of Search ........................... 424/85.2; 530/351

[56] References Cited

U.S. PATENT DOCUMENTS

| | | | |
|---|---|---|---|
| 4,518,584 | 5/1985 | Mark et al. | 424/85.1 |
| 5,215,895 | 6/1993 | Bennett et al. | 435/69.52 |
| 5,270,181 | 12/1993 | McCoy et al. | 435/69.7 |
| 5,292,646 | 3/1994 | McCoy et al. | 435/69.7 |

FOREIGN PATENT DOCUMENTS

| | | | |
|---|---|---|---|
| 9107495 | 5/1991 | WIPO . | |
| 9204455 | 3/1992 | WIPO . | |
| WO93/06840 | 4/1993 | WIPO | A61K 37/02 |

OTHER PUBLICATIONS

Teramura et al., Blood, vol. 79(2), pp. 327–331, 1992.
Yonemura et al., Br. J. Haematology, vol. 84, pp. 16–23, 1993.
Yin et al., J. Immunol., vol. 151(5), pp. 2555–2561, Sep. 1993.
Baumann et al., J. Biol. Chem., vol. 266(30), pp. 20424–20427, 1991.
Musashi et al., PNAS, vol. 88, pp. 765–769, 1991.
Zimmerman et al., Proc. Natl Acad Sci USA 72:5121 (1975).
Hoyer et al., Blood 55:1056 (1980).
Sakariassen et al., Nature 279:636 (1979).
Stel et al., Blood 65:85 (1985).
Turitto et al., Blood 65:623 (1985).
Mannucci, Blood 72(5):1449–1455 (1988).
Mannucci et al., The Lancet Ltd., pp. 869–872 (Apr. 23, 1977).
Greenberg et al., Exp. Hematol. 19:53–58 (1991).
Holzinger et al, Immunology Letters 35:109–118 (1993).
Burstein et al., Thombosis and Haemostasis 69:749 (1993).
Montgomery, Hemostasis and Thrombosis: Basic Principles and Clinical Practice, Ch. 7; 3rd Ed., J. B. Lippincott Co., Philadelphia, Pa. (1994).
Paul et al., Proc Natl Acad Sci USA 87:7512 (1990).
Sambrook et al., Molecular Cloning. A Laboratory Manual, 2d edit., Cold Spring Harbor Laboratory, New York (1989) (copy not supplied).
Yonemura, et al., Chemical Abstracts 119(13):131554g (1993).
Burstein, Stem Cells 12(4):386–393 (1994).
Neben, et al., Blood 81(4):901–908 (1993).

*Primary Examiner*—Chhaya D. Sayala
*Attorney, Agent, or Firm*—M. C. Meinert

[57] ABSTRACT

Provided by the present invention is a method for treating von Willebrand Disease (vWD) by administering IL-11. The present invention relates generally to novel methods for treating bleeding disorders and more specifically relates to methods for treating von Willebrand Disease (vWD) hemophilia A, and various hemostatic disorders such as uremia, cirrhosis, congenital platelet defects, congenital and acquired storage pool deficiency, patients with unexplained prolongations of bleeding time, as well as prophylactic treatment before surgeries.

3 Claims, No Drawings

METHODS FOR TREATING BLEEDING DISORDERS

FIELD OF INVENTION

The present invention relates generally to novel methods for treating bleeding disorders and more specifically relates to methods for treating von Willebrand Disease (vWD), hemophilia A, and various hemostatic disorders such as uremia, cirrhosis, congenital platelet defects, congenital and acquired storage pool deficiency, patients with unexplained prolongations of bleeding time, as well as prophylactic treatment before surgeries.

BACKGROUND OF THE INVENTION

Patients having von Willebrand's disease (vWD), blood coagulation disorders, such as hemophilia A, and including various hemostatic disorders such as uremia, cirrhosis, congenital platelet defects, congenital and acquired storage pool deficiency, and patients with unexplained prolongations of bleeding time, are exposed to risks of viral infection when treated with plasma derivatives. Even patients with mild forms of these disorders who normally require no supplementation with blood products are exposed to these risks when surgical procedures are undertaken.

Von Willebrand factor (vWF) is a heterogeneous, multimeric plasma glycoprotein (Zimmerman T S, Roberts J, Edgington T S: Factor VIII-related antigen: multiple molecular forms in human plasma. Proc Natl Acad Sci USA 72:5121, 1975; Hoyer L W, Shainoff J R: Factor VIII-related protein circulates in normal human plasma as high molecular weight multimers. Blood 55:1056, 1980) that plays an important role in platelet adhesion (Sakariassen K S, Bolhuis P A, Sixma J J: Human blood platelet adhesion to artery subendothelium is mediated by factor VIII/von Willebrand factor bound to the subendothelium. Nature 279:636, 1979; Stel H V, Sakariassen K S, de Groot P G, et al: von Willebrand factor in the vessel wall mediates platelet adherence. Blood 65:85, 1985; Turitto V T, Weiss H J, Zimmerman T S, et al: Factor VIII/von Willebrand factor in subendothelium mediates platelet adhesion. Blood 65:623, 1985) and also functions as the plasma binding (carrier) protein for factor VIII.

Deficiency of vWF has two consequences: platelet dysfunction and decreased concentration of factor VIII. In von Willebrand's disease (vWD), a common inherited bleeding disorder in which either the concentration or multimer pattern of vWF is abnormal, mucocutaneous bleeding related to platelet dysfunction is the predominant clinical feature. In the most common form of vWD (Type I), patients have a mild to moderate decrease in plasma vWF with a normal multimer pattern. Other forms of vWD are characterized by severe deficiencies of vWF or by abnormal multimer patterns which can be distinguished from the normal pattern electrophoretically.

Mannucci, Blood, 72(5):1449–1455 (1988), describes a non-transfusional form of treatment for congenital and acquired bleeding disorders in which desmopressin (1-desamino-8-D-arginine vasopressin; DDAVP), a synthetic analogue of the anti-diuretic hormone L-arginine vasopressin, transiently raises the circulating levels of factor VIII coagulant activity and von Willebrand factor and thereby shortens the prolonged bleeding time in patients with Type I vWD. DDAVP has been established as a non-transfusional form of treatment for mild and moderate hemophilia and von Willebrand Disease. The first clinical applications of these findings were published in 1977. Mannucci et al., The Lancet Ltd, pp. 869–872 (Apr. 23, 1977). Other treatments, such as the use of compounds such as adrenaline, vasopressin, and insulin can all induce short-term increases in endogenous factor VIII and von Willebrand factor in healthy volunteers as well as in patients with hemophilia A and vWD. Not only has DDAVP been shown to be effective in the treatment of minor bleeding episodes in patients with mild deficiency of factor VIII (hemophilia A), but also, DDAVP has shown the ability to improve bleeding times in patients with platelet dysfunction due to uremia. In all of these conditions, DDAVP is thought to transiently increase plasma vWF concentrations by stimulating the release of stored pools of vWF from vascular endothelial cells. The clinical use of DDAVP is limited by the short duration of its effect on vWF (approximately 12 hours) and a phenomenon known as tachyphylaxis (decreased response with repeat dosing).

Of general background interest to the present invention is Greenberg et al., Exp. Hematol., 19:53–58 (1991), who describe an assay of megakaryocyte maturation utilizing vWF synthesis as a marker of development. IL-6 gave increased vWF production.

Holzinger et al., Immunology Letters, 35:109–118 (1993), studied human umbilical vascular endothelial cells (HUVEC). It was found that the vWF content of these cells was reduced upon administration of IFN-γ, or IL-1. Endothelial cells are able to produce vWF. With these isolated cells, while IL-1 and IFN-γ inhibited vWF production, the other cytokines used in the study (IL-2, IL-6, GM-CSF) were not effective.

An in vivo study, Burstein et al., Thrombosis and Haemostasis, 69:749 (1993), disclose that the administration of interleukin-6 (IL-6) to dogs augments the platelet count, platelet size and plasma fibrinogen levels in normal and thrombocytopenic animals. They also observed an increase in vWF levels ranging from 2.7 to 3.6 times baseline levels between two and nine days and normalization thereafter.

Montgomery, Hemostasis and Thrombosis: Basic Principles and Clinical Practice, Ch. 7; 3rd Ed., J. B. Lippincott Co., Philadelphia, Pa. (1994) provide a summary of vWD as well as forms of treatment.

There continues to be a need in the art for alternative products in the treatment of bleeding disorders and the like.

BRIEF SUMMARY OF THE INVENTION

The present invention relates generally to novel methods for treating bleeding disorders and more specifically relates to methods for treating von Willebrand Disease (vWD), hemophilia A, and various hemostatic disorders such as uremia, cirrhosis, congenital platelet defects, congenital and acquired storage pool deficiency, patients with unexplained prolongations of bleeding time, as well as prophylactic treatment before surgeries. According to one method of the present invention, a cytokine, such as IL-11, IL-6, LIF, OSM, or CNTF, is administered in a pharmaceutically acceptable carrier to treat any of the aforementioned disorders.

DETAILED DESCRIPTION OF THE INVENTION

Provided by the present invention are methods for using a selected cytokine, such as IL-11, IL-6, LIF, OSM, or CNTF for the treatment of vWD, mild hemophilia A, and qualitative platelet defects such as occur in uremia, cirrhosis, congenital platelet defects, congenital and acquired storage pool deficiency, patients with unexplained prolongations of bleeding time, as well as prophylactic treatment before surgeries. One method of the present invention involves the administration of the cytokine, such as IL-11, and is useful in increasing vWF to a doubling of the individual's base-line levels.

Interleukin 11 (IL-11) is a pleiotropic cytokine that stimulates primitive lymphohematopoietic progenitor cells and synergizes with other hematopoietic growth factors to stimulate the proliferation and maturation of megakaryocytes. IL-11 is described in detail in International Application PCT/US90/06803, published May 30, 1991; as well as in U.S. Pat. No. 5,215,895; issued Jun. 1, 1993. A cloned human IL-11 was previously deposited with the ATCC, 12301 Parklawn Drive, Rockville, Md., on Mar. 30, 1990 under ATCC No. 68284. Moreover, as described in U.S. Pat. No. 5,270,181; issued Dec. 14, 1993; and U.S. Pat. No. 5,292,646; issued Mar. 8, 1994; IL-11 may also be produced recombinantly as a fusion protein with another protein. IL-11 can be produced in a variety of host cells by resort to now conventional genetic engineering techniques. In addition, IL-11 can be obtained from various cell lines, for example, the human lung fibroblast cell line, MRC-5 (ATCC Accession No. CCL 171) and Paul et al., the human trophoblastic cell line, TPA30-1 (ATCC Accession No. CRL 1583). Described in Proc Natl Acad Sci USA 87:7512 (1990) is a cDNA encoding human IL-11 as well as the deduced amino acid sequence (amino acids 1 to 199). U.S. Pat. No. 5,292,646, supra, describes a des-Pro form of IL-11 in which the N-terminal proline of the mature form of IL-11 (amino acids 22–199) has been removed (amino acids 23–199). As is appreciated by one skilled in the art, any form of IL-11, which retains IL-11 activity, is useful according to the present invention.

In addition to recombinant techniques, IL-11 may also be produced by known conventional chemical synthesis. Methods for constructing the polypeptides useful in the present invention by synthetic means are known to those of skill in the art. The synthetically constructed cytokine polypeptide sequences, by virtue of sharing primary, secondary, or tertiary structural and conformational characteristics with the natural cytokine polypeptides are anticipated to possess biological activities in common therewith. Such synthetically constructed cytokine polypeptide sequences or fragments thereof, which duplicate or partially duplicate the functionality thereof may also be used in the method of this invention. Thus, they may be employed as biologically active or immunological substitutes for the natural, purified cytokines useful in the present invention.

Modifications in the protein, peptide or DNA sequences of these cytokines or active fragments thereof may also produce proteins which may be employed in the methods of this invention. Such modified cytokines can be made by one skilled in the art using known techniques. Modifications of interest in the cytokine sequences, e.g., the IL-11 sequence, may include the replacement, insertion or deletion of one or more selected amino acid residues in the coding sequences. Mutagenic techniques for such replacement, insertion or deletion are well known to one skilled in the art. (See, e.g., U.S. Pat. No. 4,518,584.)

Other specific mutations of the sequences of the cytokine polypeptides which may be useful therapeutically as described herein may involve, e.g., the insertion of one or more glycosylation sites. An asparagine-linked glycosylation recognition site can be inserted into the sequence by the deletion, substitution or addition of amino acids into the peptide sequence or nucleotides into the DNA sequence. Such changes may be made at any site of the molecule that is modified by addition of O-linked carbohydrate. Expression of such altered nucleotide or peptide sequences produces variants which may be glycosylated at those sites.

Additional analogs and derivatives of the sequence of the selected cytokine which would be expected to retain or prolong its activity in whole or in part, and which are expected to be useful in the present method, may also be easily made by one of skill in the art. One such modification may be the attachment of polyethylene glycol (PEG) onto existing lysine residues in the cytokine sequence or the insertion of one or more lysine residues or other amine acid residues that can react with PEG or PEG derivatives into the sequence by conventional techniques to enable the attachment of PEG moieties.

Additional analogs of these selected cytokines may also be characterized by allelic variations in the DNA sequences encoding them, or induced variations in the DNA sequences encoding them. It is anticipated that all analogs disclosed in the above-referenced publications, including those characterized by DNA sequences capable of hybridizing to the disclosed cytokine sequences under stringent hybridization conditions or non-stringent conditions (Sambrook et al., Molecular Cloning. A Laboratory Manual, 2d edit., Cold Spring Harbor Laboratory, New York (1989)) will be similarly useful in this invention.

Also considered useful in these methods are fusion molecules, prepared by fusing the sequence or a biologically active fragment of the sequence of one cytokine to another cytokine or proteinaceous therapeutic agent, e.g., IL-11 fused to IL-6 (see, e.g., methods for fusion described in PCT/US91/06186 (WO92/04455), published Mar. 19, 1992). Alternatively, combinations of the cytokines may be administered together according to the method.

Thus, where in the description of the methods of this invention a particular cytokine is mentioned by name, it is understood by those of skill in the art that the named cytokine encompasses the protein produced by the sequences presently disclosed in the art, as well as proteins characterized by the modifications described above yet which retain substantially similar activity in restoring vWF levels or platelet function. Standard laboratory tests are utilized to monitor progress of the treatment. For example, laboratory tests for vWD are described in Montgomery, et al., supra, at pp. 143, et seq., incorporated herein by reference; vWF levels are expressed as a percent of that which is found in "normal pooled plasma" or as U/dL with normal set equal to 100 U/dL and with severe vWD defined as less than 25 U/dL.

The present invention thus involves treating patients having vWD or platelet dysfunction and involves administering an effective amount of a selected cytokine in a pharmaceutical carrier. Treatment is preferably prophylactic, but may also be at the onset of symptoms associated with the aforementioned disorders.

Suitable pharmaceutically acceptable carriers facilitate administration of IL-11 and are well known in the art. Exemplary carriers include sterile saline, lactose, sucrose, calcium phosphate, gelatin, dextrin, agar, pectin, peanut oil, olive oil, sesame oil, and water. Additionally, the carrier or diluent includes a time delay material, such as glyceryl monostearate or glyceryl distearate alone or with a wax. In addition, slow release polymer formulations can be used. Suitable sustain-release matrices contain the active ingredient in a mixture with one or more of the following: sodium bentonite, ethylcellulose, stearic acid, calcium stearate, adipic acid, fumeric acid, polyethylene glycol, deacetylated chitin, and cellulose acetate. Suitable preservatives and/or stabilizers may be included.

Alternatively, the selected cytokine, e.g., IL-11, IL-6, OSM, LIF or CNTF, can be combined with other conventional agents useful in alleviating the symptoms associated with the aforementioned disorders, other hematopoietic growth factors or DDAVP, or blood products, such as cryoprecipitate. A suitable formulation comprises, for example, in the case of IL-11; 5 mg IL-11, 3.10 mg histidine and 22.5 mg glycine, e.g., as a lyophilized powder which can be reconstituted with 1 mL sterile water for injection. As is apparent to one skilled in the art, other suitable formulations are equally effective according to the methods of the present invention.

Without wishing to be bound by theory, the inventor believes that the methods of treatment are effectuated by enhancing the synthesis and release of vWF from cells which produce it, for example, megakaryocytes, and vascular endothelial cells.

In the treatment of vWD, the IL-11 can be administered by any suitable route, but is preferably administered systemically, i.e., parenterally. Of the parenteral routes, subcutaneous and intravenous are preferred.

A suitable treatment regimen for patients undergoing treatment, including prophylactic treatment may be determined by the attending physician based upon such factors as the patient's age, sex, weight, and general health. Generally, a suitable dose of cytokine, e.g., IL-11 ranges broadly between one microgram/kilogram body weight and less than 1,000 microgram/kilogram bodyweight. Another suitable dose may be in the range of between about 10 microgram/kilogram and about 100 microgram/kilogram, and more preferably between about 10 microgram/kilogram and about 50 microgram/kilogram, and most preferably about 25 μg of IL-11 per kilogram of body weight. If desired, these doses can be adjusted to units. A unit is conventionally described as the concentration of polypeptide which leads to half-maximal stimulation in a suitable assay, e.g., for IL-11, the T1165 assay described in PCT/US90/06803. Doses may be administered daily for between one day and six months, or for as long as is deemed necessary and safe as is readily ascertained by standard tests by the attending physician, depending upon the nature of the disorder being treated. Where appropriate, the dosages may be adjusted upward or downward, for example, a dosing regimen requiring administration of IL-11 at a dose of 25 μg/kg, daily for one week, (or fewer days, or multiple weeks if indicated;) measurement of vWF levels (or whatever levels of whatever marker is customarily measured for the disorder being treated) to determine if such a dose results in an increase of vWF levels (or corresponding marker) and if not, increasing the dose two-fold for an additional time period of treatment, measurement of vWF levels (marker levels), etc., until an effective dosing regimen is reached. The adjustment of the dosages is well within the skill of the art based on the known toxicities of the cytokines useful in this invention.

The following example illustrates the methods of the present invention and in particular the use of IL-11 in increasing vWF levels. However, the examples do not limit the scope of the invention.

The plasma concentration of von Willebrand Factor (vWF) is studied in normal adult volunteers receiving recombinant human interleukin eleven (NEUMEGA™ rhIL-11 Growth Factor) or placebo in a double-blind, randomized study. Six male and six female subjects receive a single daily subcutaneous injection of either IL-11 at a dose of 25 micrograms per kilogram per day (mcg/kg/d) or an equivalent volume of placebo. Treatment with IL-11 or placebo is continued for seven days. Plasma vWF concentration and vWF multimer composition are measured at baseline (the day before treatment), on Day 3 of dosing, and on Day 8 (the day after the last dose of IL-11 or placebo). Plasma vWF concentration in the subjects receiving placebo does not change significantly during the study. In contrast, mean plasma vWF concentrations in the subjects receiving IL-11 are 79.5 (standard deviation (SD) 22.3) at baseline, 118.0 (SD 33.8) on Day 3, and 153.7 (SD 33.4) on Day 8 ($p=0.02$ for difference between treatment groups on Day 8 and $p<0.01$ for difference between Day 8 and baseline). The pattern of vWF multimers is normal in both the IL-11 and placebo groups. Platelet counts do not increase above baseline in either group.

Patients. Twelve normal adults (six males and six females), aged 18 to 40 years, comprise the study. Subjects weigh within 10% of the normal range for their height and have normal hematologic, renal, and hepatic function. Any patient is excluded if he/she:

has known sensitivity to any *E. coli* protein;

has a history of severe allergic reactions to any drug;

has any current infection requiring therapy;

has evidence of hepatitis B or C, or HIV infection;

has a history of major organ system disease, including thromboembolic disease;

has a history of drug or alcohol abuse;

has used any prescription or over-the-counter medications within a week before study entry;

has used corticosteroids or barbiturates within one month before study entry;

has used any investigational drug within two months before study entry;

has used any tobacco product within one month before study entry;

uses any hormonal form of contraception; or tests positive (urine or blood) for any commonly abused drug.

Treatment. Subjects are randomized to receive a single daily subcutaneous injection of either recombinant human interleukin eleven (NEUMEGA™ rhIL-11 Growth Factor), 25 mcg/kg/d, or an equivalent volume of placebo. NEUMEGA™ rhIL-11 is produced in *E. coli* by Genetics Institute, Inc., Cambridge, Mass. The formulation buffer (20 mM histidine, 300 mM glycine) is used as placebo. Subjects are randomly assigned to treatment by a biostatistician at Genetics Institute, Inc., with stratification by sex. Treatment assignments are not revealed to any clinical study personnel. Patients are injected once daily at approximately 10:00 am. The site of injection is rotated among sites on each subject's abdomen, flank, or thigh. Treatment is continued for 7 days.

Clinical and routine laboratory assessments. Subjects are confined to the research facility and are monitored daily by research nurses throughout the study.

Measurement of vWF and vWF multimer analysis. Plasma samples for measurement of vWF and vWF multimer analysis are drawn at baseline, on Day 3, and on Day 8. The assays for plasma vWF and multimer analysis are performed by Scripps Immunology Reference Laboratory and can be performed routinely by any clinical laboratory. Plasma vWF is measured by solid phase enzyme-linked immunosorbent assay (ELISA). Montgomery, supra. Briefly, in the method used, diluted controls, standards and patient specimens are added to a microtiter plate coated with purified antibody to von Willebrand factor. The vWF antigen present in the sample binds to the antibody on the microtiter plate. After washing, peroxidase conjugated anti-vWF is added to form a sandwich complex with the bound vWF antigen. The microtiter plate is washed again and an enzyme substrate is added to visualize the sandwich complex. The color intensity is read using an ELISA plate reader (photometer) and is proportional to the concentration of vWF antigen. Results are reported as the percent of antigen compared to a sample of normal pooled plasma. Plasma vWF multimer pattern is assessed by SDS-agarose gel electrophoresis, Western blotting, and chemiluminescent detection.

Statistical analysis. Summary statistics are generated to compare the data on plasma vWF concentration for the two treatment groups (IL-11 vs. placebo) at baseline, Day 3, and Day 8. A two-sample, two-sided t-test was performed at each time-point to test the null hypothesis (no difference in mean values for the two treatment groups). A difference is considered statistically significant if the comparison of rhIL-11 with placebo results in rejection of the null hypothesis at a p value of less than five percent ($p<0.05$). In addition, a paired t-test is used to test the percent change from baseline in plasma vWF concentration at each time-point. This test is performed separately for each treatment group.

Plasma vWF and vWF multimers. The plasma concentrations of vWF for all subjects are shown in Table 1. There is no change in the mean plasma vWF concentrations in the placebo group from baseline to Day 8. In contrast, plasma vWF concentrations progressively increase in all IL-11-treated subjects during the study. By chance, the mean plasma vWF concentration is slightly lower at baseline in the IL-11 group (79.5±22.3) compared with the placebo group (103.3±35.9). This difference is not statistically significant. However, on Day 3 the mean plasma vWF concentration in the IL-11 group (118.0±33.8) is higher than in the placebo group (93.5±31), and by Day 8, the difference between the mean vWF concentration in the IL-11 group (153.7±33.4) and the mean vWF concentration in the placebo group (97.8±37.5) is statistically significant (p=0.02). The change in vWF concentration from baseline to Day 8 in the IL-11 group is statistically significant (p<0.01). There are no abnormalities of vWF multimer pattern in any subject in either the IL-11 or placebo groups.

TABLE 1

| Plasma vWF Concentrations | | | | | |
|---|---|---|---|---|---|
| | | Patient | vWF (%) | | |
| Treatment | Sex | Number | Baseline | Day 3 | Day 8 |
| Placebo | F | 1 | 64 | 60 | 52 |
| | F | 2 | 159 | 149 | 156 |
| | F | 4 | 76 | 70 | 79 |
| | M | 7 | 133 | 101 | 127 |
| | M | 8 | 95 | 93 | 80 |
| | M | 11 | 93 | 88 | 93 |
| Mean ± SD | | | 103.3 ± 35.9 | 93.5 ± 31.1 | 97.8 ± 37.5 |
| rhIL-11 | F | 3 | 104 | 138 | 160 |
| | F | 5 | 87 | 151 | 166 |
| | F | 6 | 54 | 75 | 105 |
| | M | 9 | 60 | 118 | 173 |
| | M | 10 | 105 | 147 | 195 |
| | M | 12 | 67 | 79 | 123 |
| Mean ± SD | | | 79.5 ± 22.3 | 118.0 ± 33.8 | 153.7* ± 33.4 |

* p = .02 compared with placebo group and p < .01 compared with baseline in the IL-11 group While the present invention has been described in terms of specific methods and compositions, it is understood that variations and modifications will occur to those skilled in the art upon consideration of the present invention.

Numerous modifications and variations in the invention as described in the above illustrative examples are expected to occur to those skilled in the art and, consequently, only such limitations as appear in the appended claims should be placed thereon. Accordingly, it is intended in the appended claims to cover all such equivalent variations which come within the scope of the invention as claimed.

What is claimed is:

1. A method for increasing levels of von Willebrand Factor (vWF), comprising the step of administering an effective amount of Interleukin-11 (IL-11) in a suitable pharmaceutical carrier to increase levels of vWF.

2. The method of claim 1, comprising 10 to 100 µg IL-11 per kilogram body weight.

3. The method of claim 1, comprising 25 µg IL-11 per kilogram body weight.

* * * * *